United States Patent [19]

Gandolfi et al.

[11] Patent Number: 5,206,254

[45] Date of Patent: Apr. 27, 1993

[54] β-CARBONYL-CARBOXYAMIDES OF 1,3-THIAZOLIDINES

[75] Inventors: Carmelo A. Gandolfi; Roberto Di Domenico; Silvano Spinelli; Licia Gallico; Bruno Lumachi; Sergio Tognella, all of Milan, Italy

[73] Assignee: Boehringer Mannheim Italia S.p.A., Milan, Italy

[21] Appl. No.: 549,011

[22] PCT Filed: Mar. 2, 1989

[86] PCT No.: PCT/EP89/00205

§ 371 Date: Oct. 29, 1990

§ 102(e) Date: Oct. 29, 1990

[87] PCT Pub. No.: WO89/08648

PCT Pub. Date: Sep. 21, 1989

[30] Foreign Application Priority Data

Mar. 17, 1988 [IT] Italy .................. 19813 A/88

[51] Int. Cl.$^5$ ............. C07D 277/04; C07D 417/06; C07D 417/12; A61K 31/425
[52] U.S. Cl. .................... 514/365; 514/236.8; 514/255; 514/326; 514/342; 544/133; 544/369; 546/277; 546/209; 548/200
[58] Field of Search ............ 548/200; 546/209, 277; 544/133, 369; 514/236.8, 255, 326, 342, 365

[56] References Cited

U.S. PATENT DOCUMENTS 4,798,898 1/1989 Gandolfi .................. 548/146
4,857,643 8/1989 Gandolfi .................. 544/121

OTHER PUBLICATIONS

Fieser, Reagents for Organic Synthesis, p. 209 (1967).
R.N. 119637-67-1 Moguisteine.

*Primary Examiner*—Robert Gerstl
*Attorney, Agent, or Firm*—Nikaido, Marmelstein, Murray & Oram

[57] ABSTRACT

This application relates to compounds of formula I;

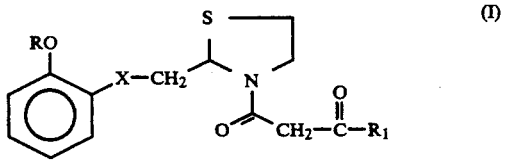

wherein R is hydrogen, a linear or branched $C_1$-$C_4$-alkyl, allyl or propargyl; X is O, $CH_2$ or S; $R_1$ is —$(CH_2)_n$Ra, hydroxy, —O—$(CH_2)_n$Ra, —NRbRc or —NH c$(CH_2)_m$—NRbRc; Ra is hydrogen, a linear or branched $C_1$-$CH_4$-alkyl, phenyl, p-methoxy-phenyl, 3,4,5-trimethoxyphenyl, B-pyryidyl, cyclopentyl or cyclohexyl; Rb and Rc, can be the same or different and are selected independently in the group of hydrogen, linear or branched $C_1$-$C_4$-alkyl, cyclohexyl, cyclopentyl, benzyl, hexahydrobenzyl, α,β or γ-pyridylmethyl; or Rb and Rc taken together with the N atom to which they are bound can form a morpholino, piperidino or piperazino residue of formula Rd—N($CH_2$—$CH_2$)$_2$—N— wherein Rd is hydrogen, linear or branched $C_1$-$C_4$-alkyl, benzyl, hexahydrobenzyl, ($C_6H_5$)$_2$CH—, (p—F—$C_6H_4$)$_2$CH or B-pyridylmethyl; n is zero or an integer from 1 to 3 and m is 2 or 3; and a process for the preparation thereof.

7 Claims, No Drawings

β-CARBONYL-CARBOXYAMIDES OF 1,3-THIAZOLIDINES

The present invention relates to β-carbonylcarboxyamides of 2-substituted thiazolidines, to a method for their preparation and to pharmaceutical compositions containing them.

3-acyl-2-substituted-thiazolidines, sharing both antitussive and mucus-regulating activities have been disclosed in EP-A-169,581.

The mucus-regulating activity is common to all the compounds of said EP application, while the antitussive activity depends on the N-acyl substituent of the 1,3-thiazolidine ring: when the N-acyl-substituents are oxalic, succinic, glutaric and cyclopropyl carboxylic acid residues, antitussive activity is lost.

It has now been surprisingly found, that 3-acyl-2-substituted-1,3-thiazolidines whose N-acyl-substituent is that of a β-carbonyl acid, for example a malonic acid residue, are endowed with potent and selective antitussive activity.

The present invention relates to β-carbonyl-carboxyamides of formula (I)

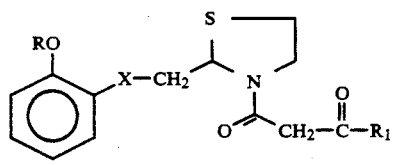

wherein
R is hydrogen, a linear or branched $C_1$–$C_4$-alkyl, allyl or propargyl;
X is O, $CH_2$ or S;
$R_1$ is selected from the group consisting of —$(CH_2)_n$Ra, hydroxy, —O—$(CH_2)_n$Ra, —NRbRc, —NH—$(CH_2)$m-NRbRc;
Ra is hydrogen, a linear or branched $C_1$–$C_4$-alkyl, phenyl, p-methoxy-phenyl, 3,4,5-trimethoxy-phenyl, β-pyridyl, cyclopentyl or cyclohexyl;
each of Rb and Rc, that are the same or different, may be hydrogen, linear or branched $C_1$–$C_4$-alkyl, cyclohexyl, cyclopentyl, benzyl, hexahydrobenzyl, α, β, γ-pyridylmethyl, or Rb and Rc taken together with the nitrogen atom to which they are linked, form a morpholine, piperidine or piperazine residue of formula Rd—N($CH_2CH_2$)$_2$N— wherein Rd is hydrogen, linear or branched $C_1$–$C_4$-alkyl, benzyl, hexahydrobenzyl, ($C_6H_5$)$_2$CH—, (p—F—$C_6H_4$)$_2$-CH— or β-pyridylmethyl;
n is zero or an integer from 1 to 3 and m is 2 or 3.

Compounds of formula (I) have at least a chiral carbon atom and have therefore more than one enantiomer. The invention includes all said enantiomers and the mixtures thereof, racemates included. Moreover, since compounds of formula (I) may contain acid or basic groups, also salts with pharmaceutically acceptable acids or bases are included in the present invention.

Pharmaceutically acceptable salts of the compounds of formula (I) with pharmaceutically acceptable bases are salts with either organic bases such as, for example, methylamine, dimethylamine, trimethylamine, lysine, arginine, N-methyl-N-cyclohexylamine, ethylamine, diisopropylamine, tromethamine, N,N-dimethylethanolamine, N,N-diethylethanolamine or β-phenylethylamine, morpholine, piperidine, piperazine, galactosime, N-methylglucamine or inorganic bases such as, for example, alkaline or alkaline-earth hydroxides as well as zinc or aluminum hydroxydes.

Pharmaceutically acceptably salts of the compounds of formula (I) with pharmaceutically acceptable acids are salts with either organic acids such as, for example, acetic, formic, propionic, fumaric, maleic, malic, malonic, tartaric, benzoic, salicyclic, methanesulphonic, lactic, asparatic, glutammic, L or D-2-phenyl-thiazolidinecarboxylic acids, N-acetyl-crysteine or inorganic acids such as, for example, nitric, phosphoric, hydrochloric, hydrobromic acids.

Specific examples of compounds of the invention are the following:
(R,S)-2-(2-methoxy-phenoxymethoxy)-3-ethoxycarbonylacetyl 1,3-thiazolidine;
(R,S)-2-(2-methoxy-phenoxymethyl)-3-carboxyacetyl-1,3-thiazolidines;
(R,S)-2-(2-methoxy-phenoxymethyl)-3-(3-oxo-butanoyl)-1,3-thiazolidines;
(R,S)-2-(2-methoxy-phenoxymethyl)-3-(3-β-pyridyl-3-oxo-propanoyl)-1,3-thiazolidine;
(R,S)-2-(2-methoxy-phenylthiomethyl)-3-(3-phenyl-3-oxo-propanoyl)- 1,3-thiazolidine;
(R,S)-2-(2-methoxy-phenyl)ethyl-3-(3-cyclohexyl-3-oxo-propanyl)-1,3-thiazolidine;
N-β-pyridylmethyl, N'-[(R,S)-2-(2-methoxy-phenoxymethyl)-1,3-thiazolidine]-malondiamide;
N-β-pyridylmethyl, N'[(+)-2-(2-methoxy-phenoxymethyl-1,3-thiazolidine]-malondiamide;
N-β-pyridylmethyl, N'-[(−)-2-(2-methoxy-phenoxymethyl)-1,3-thiazolidine]-malondiamide;
N-β-pyridylmethyl, N'-[(R,S)-2-(2-allyloxy-phenoxymethyl)-1,3-thiazolidine)-malondiamide;
N-β-pyridylmethyl, N'-[(R,S)-2-(2-propargyloxy-phenoxymethyl)-1,3-thiazolidine]-malondiamide;
N-β-pyridylmethyl, N'-[(R,S)-2-2-(2-methoxy-phenyl-thiomethyl)-1,3-thiazolidine]-malondiamide;
N-β-pyridylmethyl, N'-[(R,S)-2-(2-methoxy-phenyl)ethyl-1,3-thiazolidine]-malondiamide;
N-methyl-N'-[(R,S)-2-(2-methoxy-phenoxymethyl)-1,3-thiazolidine]-malondiamide;
N-2-(diethylamino)ethylamino-N'-[(R,S)-2-(2-methoxy-phenoxymethyl)-1,3-thiazolidine]-malondiamide;
N-(4-methyl-piperazin-1-yl)-N'-[(R,S)-2-(2-methoxy-phenoxymethyl)-1,3-thiazolidine]-malondiamide;
N-morpholin-N'-[(R,S)-2-(2-methoxy-phenylthiomethyl)-1,3-thiazolidine]-malondiamide;
N-piperidin-N'-[(R,S)-2-(2-methoxy-phenyl)-ethyl-1,3-thiazolidine]-malondiamide.

The compounds of the invention are prepared by a process comprising the reaction of a compound of formula (II)

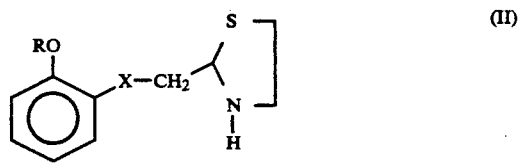

wherein R and X are as above defined, with an acid or with an activated species of an acid of formula (III)

to give a compound of formula (Ia)

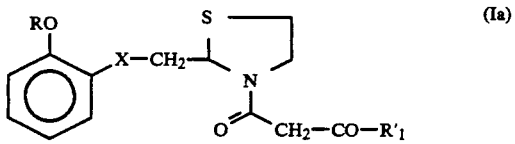

wherein $R'_1$ is as above defined for $R_1$, or is a group convertible into $R_1$, and if desired, converting a compound of formula (Ia) when $R'_1$ is different from $R_1$ and/or, if desired, converting a compound of formula (I) into another compound of formula (I) when $R'_1$ is the same of $R_1$ and/or, if desired, salifying and/or solvating a compound of formula (I), and/or, if desired, obtaining a compound of formula (I) from a salt thereof and/or, if desired, separating a mixture of isomers into the single isomers.

Suitable activated species of an acid of formula (III) are acyl chlorides or anhydrides. Alternative suitable species are mixed anhydrides between an acid of formula (III) and benzyl and/or alkylchloroformates; and azides or imidazolides of an acid of formula (III).

Using well-known methods, a compound of formula (II) can be reacted:

a) with an acyl chloride of an acid of formula (III) in the presence of an organic or inorganic base;

b) with an acid of formula (III) in the presence of dicyclohexylcarbodiimide, N-dimethylaminopropyl-N'-ethylcarbodiimide or carbonyldiimidazole;

c) with a mixed anhydride generated "in situ" by reacting an acid of formula (III) with a benzyl and/or alkyl chloroformate, for instance ethylchloroformate.

Since a compound of formula (Ia) and/or (I) if desired, can be converted into another compound of formula (I), by exchange of the appropriate $R_1$ substituent, it is clear that some compounds of formula (I) and/or (Ia) are intermediates useful for the preparation of other compounds of the present invention: for example, using reactions with a suitable amine and/or alcohol, a free carboxylic group of a compound of formula (I) or (Ia) may be transformed into an ester or carboxyamide group.

In general, the above mentioned procedure yields racemic mixtures, whereas the use of chiral amines or alcohols yields mixtures of diastereoisomers. If desired, such diastereoisomers mixtures may be subsequently separated into the single isomers by usual methods, e.g. column chromatography.

Pharmaceutically acceptable salts of a compound of formula (I) are obtained by reaction of an acid of formula (I) with an appropriate inorganic and/or organic base and/or by treatment of a basic compound of formula (I) with an organic or mineral acid.

Solvates of compounds I can be obtained by crystallization or recrystallization from a solvent; for example, hydrates can be obtained by crystallization or recrystallization from water, or from mixtures of organic solvents with water.

Moreover, salts or solvates of compounds (I), that are not pharmaceutically acceptable, may be useful intermediates in the production of pharmaceutically acceptable salts or solvates; consequently, non-pharmaceutically acceptable salts or solvates are also included in the scope of the present invention. As above cited, the compounds of formula (I) are chiral substances and the process of the invention produces (R,S) mixtures. Single enantiomers may be obtained by optical resolution using both optically active acids and/or bases; alternatively, single enantiomers may be prepared by asymmetrical synthesis.

The acylation reaction of a compound of formula (II) with an acylating agent of formula (III) can be carried out by reaction in an inert solvent, using stoichiometric quantities of reagents or using a slight excess of the acylating agent, optionally in the presence or in the absence of a base.

When a compound of formula (II) is used as a pure enantiomer, this compound is preferably reacted as a salt in the presence of from catalystic to stoichiometric amounts of a base such as an alkylamine, imidazole, 4-dimethylaminopyridine and so on.

Diketene, i.e. the internal enolester of the acetylacetic acid, is the preferred activated species of said acid of formula (III) ($R'_1$=$CH_3$) used in the reaction of a compound of formula (II) to obtain a compound of formula (Ia) wherein $R'_1$ is methyl.

Preferred inert solvents are halogenated solvents such as 1,2-dichloroethane, methylene chloride, chloroform; esters such as ethyl acetate and ethyl formate; ketones such as acetone and methylethylketone; ethers such as diethylether, 1,2-dimethoxyethane, dimethylale, dioxane, tetrahydrofuran and mixtures thereof, in the presence or in the absence of the water.

Counter-bases used during the acylation reaction may be alkaline or alkaline-earth hydroxides, carbonates or bicarbonates, or organic bases such as pyridine, trimethylamine, 4-dimethylamino pyridine, imidazole.

The acylation reaction is preferably carried out at temperatures ranging from $-10°$ C. to reflux temperature of the solvent, but the preferred temperature interval ranges from $-10°$ C. to the room temperature; the reaction times range from few minutes to three days, usually from 30 minutes to 4-5 hours.

The compounds of formula (II) have been disclosed in U.K. Patent applications No: 84-19254 (27.7.1984) and No. 85-17553 (11.7.1985).

The compounds of formula (III) are known compounds or are prepared according to known methods. Some compounds of formula (III) are commercially available, such as diketene, malonyl chloride or alkoxymalonyl chloride.

Monoamides of malonic acids of formulae (IVa) and (IVb)

wherein Rb, Rc and m are as above defined, may be obtained by reaction of an alkoxymalonylchloride with an amine RbRcNH and/or RbRc—N—$(CH_2)_m$—$NH_2$, followed by saponification of the ester group or by reaction of malonyl chloride with a molar equivalent of the amine in the presence of an excess of aqueous solution of an above mentioned inorganic base, so as to hydrolyze the intermediate monoamide malonylchloride to the monoamide malonic acid.

The compounds of the invention can be used as long-lasting antitussive agents.

The long lasting antitussive activity of the compounds of the invention is particularly unexpected, in account of the fact that the acylating residue $R_1$—CO—$CH_2$—CO— of the 1,3-thiazolidines of the present invention is part of a particular subgroup of the acyl residue of formula $R'_1—CO—(CH_2)_{m'}—CO—$ already claimed in EP-A 169,581.

The acyl 1,3-thiazolidines disclosed in EP-A 169,581, wherein $m_1$ of $R'_1—CO—(CH_2)_{m'}—CO—$ is zero and/or the integer 2,3 possess only a selective mucus-regulating activity while the compounds of the present invention wherein $m_1$ is the integer 1, are provided with antitussive activity, which is completely lacking in the known higher or lower homologue compounds.

As antitussive properties, inhibiting the mucus expectoration, can be undesirable in a mucus regulating substance, analogously mucus-regulating properties might be unnecessary or useless in an antitussive substance. Therefore the selective antitussive activity of the compounds of formula (I) is a desirable therapeutic target.

The compounds of the invention are therapeutically useful substances, practically free of acute, subacute or chronic toxic effects. $LD_{50}$ values, usually exceeding 1 g/kg body weight are measured in mice and in rats after oral and intraperitoneal (i.p.) administration of the compounds of the invention. Only N-diethylaminoethylamino, N'-[(R,S)-2-(2-methoxyphenoxymethyl)-1,3-thiazolidine]-malondiamide and N-β-pyridylmethylamino-N'-[(R,S)-2-(2-methoxy-phenoxy-methyl)-1,3-thiazolidine]-malondiamide show $DL_{50}$ values of 0.25 and 0.85 g/Kg respectively after oral administration to rats at the 14th day of observation.

The technique described by Charlier et al., (Arch. Int. Pharmacodyn., 134, 306, 1961), adapted with minor modifications, is used to investigate the antitussive properties of the compounds of the invention.

The protective action of these substances against cough strokes induced by exposure to citric acid aerosol, is evaluated in animals (guinea pigs) after oral and subcutaneous administration.

Cough strokes are induced in animals by exposure to 7.5% aqueous citric acid aerosol. Each animal is also used as a control animal; the aerosol exposure for a 5 minutes period is performed both 24 hours before and one hour after the drug administration.

For each dose level, a group of six (male) animals is treated; the total number of cough strokes are recorded both for each animal and for each dose level.

The pharmacological activity (i.e. the antitussive protective effect) of a drug is evaluated on the basis of the percentual reduction of the number of cough strokes after drug administration in comparison with the number of cough strokes, registered for each animal 24 hours before the drug administration (i.e. in the absence of the drug). The pharmacological effects of the compounds of the invention are dose-related. Codeine phosphate (CP) has been used as positive reference standard; a 30 mg/Kg dose level of CP causes a 50% reduction in the treated animals.

To better define the invention and the peculiar antitussive properties of the compounds of formula (I), the results of a direct comparison of the compound of the invention with some strictly related acyl-1,3-thiazolidines, disclosed in EP-A-160,581, are reported in Table 1; all the substances and codeine phosphate, as internal standard, are administered by oral route at the dose level of 30 mg/kg.

The comparison shows that the compounds of formula (i) exhibit pronounced protective effects at least similar or higher than the positive reference standard in opposition to the poor effect shown by the compounds already disclosed, from 2 to 4. It should be pointed out that compounds 7 and 10 of the invention are practically equiactive after subcutaneous administration, since a long lasting percent reduction (respectively 90 and 83%) is observed at the dose level of 60 mg/Kg. This behaviour is different from that of the acetyl derivative (1) of EP-A 169.581, whose effect rapidly declines in time from a 40% value to a 25% value, 2 hours after the administration.

Table 2 refers to results with the compounds of formula (I) in the electrically stimulated cough stroke test, in comparison with codeine phosphate.

Cough strokes are provoked by electrical stimulation of the guinea pig tracheal mucosa. according to Cavanaugh et al., (Arch. Ing. Pharmacodyn., 220, 258, 1976). Cough strokes are stimulated both before (i.e. in the absence of drug treatment) and one hour after the drug administration. Also in this case, the drug activity is measured for each animal evaluating the percent reduction of the number of cough strokes after drug administration in comparison with the basal values in the absence of drug treatment. A group of six animals is used at each dose level; this test is particularly useful for the evaluation of long lasting effects until and after three hours from the administration.

TABLE I

| | Substances: 3-acyl-2-(2-methoxy phenoxymethyl)-1,3-thiazolidine (dosage 30 mg/Kg os) | Percent reduction cough strokes | $ED_{50}$ mg/kg |
|---|---|---|---|
| 1 | $CH_3—CO—$ | 40 | |
| 2 |  | 12 | |
| 3 | $C_2H_5O—CO—CO—$ | 18 | |
| 4 | $C_2H_5O—CO—(CH_2)_2—CO—$ | 22 | |
| 5 | $C_2H_5O—CO—(CH_2)_3—CO—$ | 17 | |
| 6 | $CH_3CO—CH_2—CO—$ | 45 | 30 |
| 7 | $(\pm)C_2H_5OCO—CH_2—CO$ | 51 | |
| 8 | $(+)C_2H_5OCO—CH_2—CO—$ | 66 | |
| 9 | $(-)C_2H_5OCO—CH_2—CO—$ | 64 | |
| 10 | $HOCO—CH_2—CO—$ | 35 | |
| 11 | $CH_3NH—CO—CH_2—CO—$ | 65 | |
| 12 |  | 56 | |

TABLE I-continued

| Substances: 3-acyl-2-(2-methoxy phenoxymethyl)-1,3-thiazolidine (dosage 30 mg/Kg os) | Percent reduction cough strokes | ED$_{50}$ mg/kg |
|---|---|---|
| 13  CH$_3$—N⟨   ⟩N—CO—CH$_2$—CO— 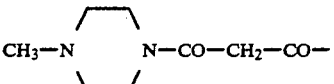 | 57 | |
| 14  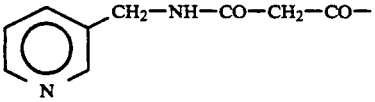 CH$_2$—NH—CO—CH$_2$—CO— | 78 | 14 |
| Codeyne phosphate | 50 | 30 |
| 15  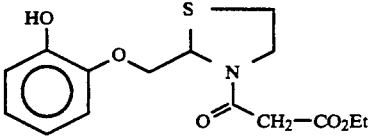 | 58 | |

TABLE II

| Substances: dosage 15 mg/Kg os 3-acylthiazolidine-2-(2-methoxy phenoxymethyl)-1,3-thiazolidine (dosage 15 mg/kg os) | Percent reduction of cough strokes | ED$_{50}$ mg/kg |
|---|---|---|
| 1  CH$_3$—CO— | 12 | |
| 2  —CO— | n.a. | |
| 3  EtO—CO—CO— | n.a. | |
| 4  (±)EtO—CO—CH$_2$—CO— | 62 | 11 |
| 5  (+)EtO—CO—CH$_2$—CO— | 78 | |
| 6  (−)EtO—CO—CH$_2$—CO— | 14 | |
| 7  CH$_3$NHCO—CH$_2$—CO— | 18 | |
| 8  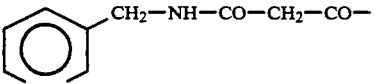 CH$_2$—NH—CO—CH$_2$—CO— | 63 | 12 |
| Codeyne phosphate | 58 | |

The results showing the long lasting persistance of the antitussive action is reported in Table 3 in comparison with codeine phosphate; all the substances are administered at 30 mg/Kg by oral route.

TABLE III

| Substances: dosage 30 mg/Kg os 3-acyl-2-(2-methoxyphenoxy-methyl)-1,3-thiazolidine | Percentage reduction of cough strokes during treatment | | |
|---|---|---|---|
| | 1 h | 2 h | 3 h |
| EtO—CO—CH$_2$—CO— | 70 | 60 | 40 |
| ⟨pyridyl⟩CH$_2$—NH—CO—CH$_2$—CO— | 80 | 67 | 60 |
| CH$_3$NH—CO—CH$_2$—CO— | 24 | 48 | 60 |
| Codeine phosphate | 77 | 53 | 46 |

The compounds of the invention are particularly effective in preventing cough strokes, generated by different stimuli. The protective effects are, in particular long lasting and both from a qualitative and quantitative point of view, the therapeutic efficacy is comparable with that of codeine phosphate, a recognized reference drug in antitussive drug investigations.

Since the compounds of the invention do not show binding affinity to opiate receptors, being unable to displace [H$_3$]-naloxone from its membrane binding sites, their mechanism of action is different from that of codeine.

In "vivo" experiments with naloxone show that this substance at a dose level of 5 mg/kg (by subcutaneous treatment, s.c.) is unable to protect guinea pig against cough strokes, evokated by the two experimental models.

While animal pretreatment with naloxone (5 mg/Kg; s.c.) completely abolishes the protective effect of a subsequent treatment with codeine phosphate (30 mg/Kg, o.s.) a subsequent treatment with (R,S)-2-(2-methoxyphenoxymethyl-3-ethoxycarbonylacetyl-1,3-thiazolidine per os at a dose level of 30 mg/Kg causes a complete protection against cough strokes induced by both experimental models.

Therefore the compounds of the invention may be therapeutically useful as antitussive agents without the typical limitations of the opiate receptors binding substances.

In addition, the compounds of formula (I) are endowed with novel, surprising and peculiar properties; these substances are able to prevent and/or to reduce the airway hyperreactivity, a clinical symptom often observed in asthmatic patients, i.e. the abnormal contractility of the bronchial smooth muscles after exposure to external stimuli as well as physical exercise, inhalation of fog, pollutants, allergens and autacoids.

In order to show this surprising pharmacological property, the compounds of the invention were tested in a bronchial hyperreactivity animal model recently developed (see Omini C. et al., 23rd Ann. Med: S.E.P.C.R., Athens 20–24th June 1988, Abstract 15S Eur. J. Resp. Dis. in press).

The airways hyperreactivity is measured as abnormal increase of the pulmonary inflation pressure (PIP) caused by the exacerbate bronchconstrictive response that follows to an autocoid challenge after active forced tobacco smoke exposure for a 10 minutes period. The abnormal PIP increase is compared with the PIP increase observed, in the same animal, before tobacco smoke, and after autacoids challenge. Male guinea pigs (400–450 g b.w.) anaesthetized with ethylurethane and pancuronium bromide were used; the recording of PIP is performed in accordance with Konzett and Rossler methods (Naumm. Schiedeberg Arch. Exp. Path/Pharmacol. 195, 71, 1940). To evidentiate such bronchial smooth muscle hyperreactivity suitable autocoids are acetylcholine, histamine, serotonine, bradykinins.

Corticosteroids, for example 6α-methyl-prednisolone- 21-hemisuccinate sodium salt (6 MPHE) (10–50 mg/Kg b.w., by i.m. route, 7 hours before tobacco smoke exposure), are effective drugs and are used as positive reference substances.

Dichromoglycate (DSCG) (20–100 mg/Kg b.w., by i.m. route, treatment 2 hours before smoke exposure) and salbutamol (0.5 mg/Kg b.w., by i.v. route, treatment 20 minutes before smoke exposure) are also effective drugs and may be used as positive reference drugs, too.

Cytologic studies of the bronochoalveolar lavage (BAL) fluids of the animals, exposed to tobacco smoke and untreated with drugs, show a statistically significant increase of the overall cell counts. Specifically, the number of epithelial cells and of eosinophils is increased, in respect to the cell content of unexposed animals.

Effective doses of 6 MPHE (50 mg/KG) and of DSCG (100 mgKg), preventing airway hyperreactivity, are also able to normalize the cellular pattern in the BAL fluids of the treated, smoke-exposed animals.

By contrast, salbutamol at its full effective dose (0.5 mg/Kg) in the hyper-reactive reaction fails to modify the smoke induced pathological changes of the BAL fluid cytology.

(R,S)-2-[2-methoxy-phenoxymethyl)-3-ethoxycarbonylacetyl-1,3-thiazolidine, (R,S)-2-(2-methoxyphenoxymethyl]-3-carboxyacetyl-1,3-thiazolidine, and N-β-pyridylmethyl, N'-[(R,S)-2-(2-methoxyphenoxymethyl)-1,3-thiazolidine]-malondiamide are significative examples of the compounds of formula (I) that are effective inhibitors of the hyperreactive reaction when tested by oral route in a dose range from 20 to 60 mg/Kg and/or by intravenous route in a dose range from 0.25 to 5- mg/Kg and/or by subcutaneous route from 2 to 15 mg/Kg.

Using the same administration route and at the same doses, the pharmacological treatment also normalizes the cytologic pattern of BAL fluids of animals exposed to tobacco smoke.

The changes of the BAL cytologic pattern (more than double epithelial cell and eosinophil increase) after exposure to forced active tobacco smoke observed in those animals mimic the events observed in human smokes (asthmatic or not) and are thought to be a clear-cut and unambiguous indication of a serious inflammatory status of the airway tissues. Therefore, the ability of the compounds of the invention to normalize cell count and cytologic pattern of BAL fluids maybe of particular relevance and utility from the therapeutical point of view. Thus, the compounds of formula (I) may be particularly useful not only as antitussive drugs but also in the treatment of airway inflammatory diseases such as for example acute and subacute bronchitiis, chronic bronchial obstructive diseases and related pathologies.

The property of normalizing BAL cytology and of preserving the pronounced and exacerbate contractility of the bronchial smooth muscle due to the challenge by external stimuli, shared by the compound of formula (I) with corticoids and DSCG, makes them of potential therapeutical utility in the prophylactic treatment of asthmatic patients to relieve pain and bronochoconstrictive attacks.

The compounds of the invention may be administered by oral, sublingual, intravenous, subcutaneous, intramuscular, rectal or inhalatory route.

The inhalatory route is particularly preferred when the treatment of airway hyperreactivity is requested. The preferred doses of the compounds range from 0.05 to about 5 mg/Kg/day, according to the patient's conditions, weight, age and administration route. The preferred dosages by inhalatory route range from 0.02 to 1 mg/Kg/day.

Higher dosages, also for prolonged periods, are not counterindicated, in consideration of the limited toxicity of the compounds of the invention. The compounds of the invention can be therapeutically used in the most convenient pharmaceutical preparations, using conventional techniques and excipients, as described in "Remington's Pharmaceutical Sciences Handbook", Hack Publ. Co. New York, U.S.A. Examples of said compositions include capsules, tablets, packets, syrups, drinkable solutions, suppositories, vials for parenteral or inhalatory administration, controlled-release devices. etc.

The following examples illustrate but do not limit the present invention.

EXAMPLE 1

Under vigorous stirring, 8 ml of an aqueous solution of $KHCO_3$ (2.65 g) are added to a solution of a 2-substituted-1,3-thiazolidine, e.g. (R,S)-2-(2-hydroxyphenoxymethyl)-1,3-thiazolidine (5.3 g) in ethyl acetate (50 ml), cooled at 0°–5° C. A solution of ethylmalonylchloride (3.2 ml) in ethyl acetate (10 ml) is added dropwise in a period of 30 minutes and the mixture is stirred for further 30 minutes. The organic and aqueous phases are separated; the organic phase is washed with 2N $H_2SO_4$ (2×50 ml), $H_2O$ (3×5 ml), 10% aqueous ammonia (3 ×(ml) and dried on $Na_2SO_4$ (2.5 g). After evaporation of the solvent under vacuum, the oily residue is crystallized from isopropyl ether, to obtain 6.4 g of:
(R,S)-2-(2-hydroxy-phenoxymethyl)-3-ethoxycarbonylacetyl-1,3-thiazolidine, m.p. 61°-63° C.

Using the same procedure, the following:
(R,S)-2-(2-methoxy-phenoxymethyl)-3-ethoxycarbonylacetyl-1,3-thiazolidine, m.p. 64°-66° C.;
(R,S)-2-(2-methoxy-phenylthiomethyl)-3-ethoxycarbonylacetyl-1,3-thiazolidine;
(R,S)-2-(2-methoxy-phenyl)-ethyl-3-ethoxyarbonylacetyl-1,3-thiazolidine;
(R,S)-2-(2-allyloxy-phenoxymethyl)-3-ethoxycarbonylacetyl-1,3-thiazolidine;
(R,S)-2-(2-propargyloxy-phenoxymethyl)-3-ethoxycarbonylacetyl-1,3-thiazolidine,
are obtained.

EXAMPLE 2

Under vigorous stirring, 200 ml of an aqueous solution of $KHCO_3$ (107 g) are added to a solution of (R,S)-2-(2-methoxy-phenoxymethyl)-1,3-thiazolidine (200 g) in ethyl acetate (21 ml), cooled at 0°-5° C.; then 97.2 ml of methylmalonylchloride are added dropwise in one hour. After one hour, the organic and aqueous phases are separated. The organic phase is washed with 2N $H_2SO_4$. After concentration of the solution to a volume of 200 ml, the crystallized solid is filtered and dried under vacuum (40° C., 15 mmHg), to give 256 g of (R,S)-2-(2-methoxyphenoxy-methyl)-3-methoxycarbonylacetyl-1,3-thiazolidine, m.p. 84°-85° C.

EXAMPLE 3

A solution of ethyl malonylchloride (1.28 ml) in ethyl acetate (6 ml) is added to a stirred suspension of (+)-2-(2-methoxy-phenoxymethyl)-1,3-thiazolidinium-D-0,0'-dibenzoyltartrate (5.8 g) in ethylacetate (40 ml), cooled at 0° C.

The mixture is stirred to give after about 2 hours a clear solution, then it is treated with an aqueous saturated $NaHCO_3$ solution (100 ml) and furtherly stirred for 15 minutes.

The organic and aqueous phases are separated, the organic phase is washed with water and anidrified on $Na_2SO_4$. After solvent removal in vacuum, the chromatographic purification of the oily-residue on $SiO_2$ (50 g; eluents hexane-ethyl acetate 2:1) affords N,N'-(+)-[2-(2-methoxy-phenoxy-methyl)-1,3-thiazolidine]-malondiamide (80 g) and (+)-[2-(2-methoxyphenoxymethyl)-3-ethoxycarbonyl]-1,3-thiazolidine (1.5 g), m.p. 62°-64° C. $[\alpha]_D = +74.3°$ (C=2.8% EtOH).

EXAMPLE 4

(−)-2-(2-methoxy-phenoxymethyl)-3-ethoxycarbonyl-1,3-thiazolidine, m.p. 64°-65° C. $[\alpha]_D = -78°$ C. (C 2.2% EtOH) is prepared using in the procedure of example 3 the (−)-2-(2-methoxy-phenoxymethyl)-1,3-thiazolidine-L-O,O'-dibenzoyl-tartrate.

EXAMPLE 5

In a 40 minutes period, a malonylchloride ($ClCO-CH_2-COCl$, 10 ml) solution in ethylacetate (10 ml) is added to a vigorously stirred mixture, cooled at 0°-10° C. of an aqueous solution (25 ml) of $K_2CO_3$ (22 g) and of an ethyl acetate (200 ml) solution of (R,S)-2-(2-methoxy-phenoxy-methyl)-1,3-thiazolidine; after one hour, aqueous N NaOH (25 ml) and water (100 ml) are added to the mixture that is stirred for additional 30 minutes.

The phases are separated and the organic layer, after re-extraction with 0.5 N NaOH, is discarded.

The combined alkaline aqueous phases are acidified to pH 2 with aqueous 37% HCl and then extracted with ethyl acetate. From the combined organic phases after water (2× 25 ml) washings, drying over $Na_2SO_4$ and concentration to small volume, a crystalline solid of (R,S)-2-(2-methoxy-phenoxymethyl)-3-carboxyacetyl-1,3-thiazolidine (m.p. 120°-122° C.) is collected by filtration.

EXAMPLE 6

A mixture of 25 g of (R,S)-2-(2-methoxyphenoxymethyl)-3-ethoxycarbonylacetyl-1,3-thiazolidine and of aqueous 1N NaOH (75 ml) in ethanol (250 ml) is stirred for 30 minutes at room temperature to give before a clear solution and after precipitation of a crystalline solid, the suspension is cooled to 0° C. and stirred for one additional hour. The crystalline precipitate is filtered and dried obtaining 20.5 g of (R,S)-2-(2-methoxyphenoxymethyl)-3-carboxyacetyl-1,3-thiazolidine, sodium salt, m.p. 78°-81° C.

The filtered liquid is concentrated and acidified to pH 4.2 with 2N $H_2SO_4$ to give 4.2 g of (R,S)-2-(2-methoxyphenoxymethyl)-3-carboxyacetyl-thiazolidine.

EXAMPLE 7

The following compounds are prepared by acylation of a 2-substituted thiazolidine with malonyl chloride using the procedure outlined in example 5 or by saponification using the procedure in example 6 starting from a 3-alkoxy-carbonylacetyl-thiazolidine prepared according to the procedures outlined in examples 1, 2 and 3:
(R,S)-2-(2-methoxy-phenylthiomethyl)-3-carboxyacetyl-1,3-thiazolidine;
(R,S)-2-(2-allyloxy-phenoxymethyl)-3-carboxyacetyl-1,3-thiazolidine;
(R,S)-2-(2-propargyloxy-phenoxymethyl)-3-carboxyacetyl-1,3-thiazolidine;
(R,S)-2-(2-methoxy-phenyl)-ethyl-3-carboxyacetyl-1,3-thiazolidine;
(+)-2-(2-methoxy-phenoxymethyl)-3-carboxyacetyl-1,3-thiazolidine;
(−)-2-(2-methoxy-phenoxymethyl)-3-carboxyacetyl-1,3-thiazolidine.

EXAMPLE 8

0.3 ml of 96% $H_2SO_4$ are added to a solution of (R,S)-2-(2-methoxy-phenoxymethyl)-3-carboxy-acetyl-1,3-thiazolidine (3 g) in 30 ml of 2-propanol. The mixture is heated for 2 hours to the reflux temperature, concentrated to a small volume and the residue is divided between water and ethyl acetate.

The organic phase is washed with water, 5% $NaHCO_3$ and water, anidrified over $Na_2SO_4$ and the solvent is evaporated under vacuum. The residue is purified by column chromatography ($SiO_2$; hexane-ethyl acetate 2:1) to obtain 2 g of (R,S)-2-(2-methoxy-phenoxymethyl)-3-acetyl-1,3-thiazolidine.

EXAMPLE 9

Dicyclohexylcarbodiimide (3.46 g) is added to a solution of β-pyridylmethylamine (1.63 ml) and of (R,S)-2-(2-methoxy-phenoxymethyl)-3-carboxyacetyl-1,3-thiazolidine (5 g) is anhydrous dichloroethane (50 ml). The mixture is stirred for 2 hours and the precipitate of N,N-dicyclohexylurea is filtered. After extraction with 5% aqueous NaHCO₃ (2×10 ml), water (2×10 ml) and 4N H₂SO₄ (3×25 ml), the organic phase is discarded. The combined acid aqueous extracts are alkalinized to pH 8.5 with 20% aqueous NaOH and extracted with ethyl acetate (3×20 ml). The combined organic phases after water washings, drying over Na₂SO₄, evaporation under vacuum give an oily residue of N-β-pyridylmethyl, N'[(R,S)-2-(2-methoxy-phenoxymethyl]-1,3-thiazolidine malondiamide (5.6 g).

A solution of this compound (4.73 g) in ethyl acetate (40 ml) is treated with a methanol (14 ml) solution of fumaric acid (1.37 g). The mixture is filtered, diluted with diethyl ether (150 ml), cooled 0°–5° C. for 2 hours to give N-β-pyridylmethyl, N'[(R,S)-2-(2-methoxyphenoxymethyl)-1,3-thiazolidine]-malondiamide hemifumarate.

Using the same procedure, the following compounds are prepared:
N-β-pyridyl-methyl-N'-[(+)-2-(methoxyphenoxymethyl)-1,3-thiazolidine]-malondiamide;
N-β-pyridylmethyl, N'-[(−)-2-methoxyphenoxymethyl)-1,3-thiazolidine]-malondiamide;
N-β-pyridylmethyl, N'-[(R,S)-2-allyloxy-phenoxymethyl)-1,3-thiazolidine]-malondiamide;
N-β-pyridylmethyl, N'-[(R,S)-2-propargyloxy-phenoxymethyl)-1,3-thiazolidine]-malondiamide;
N-β-pyridylmethyl, N'-[(R,S)-2-methoxy-phenylthiomethyl)-1,3-thiazolidine]-malondiamide;
N-β-pyridylmethyl, N'[(+)-2-methoxyphenyl)-1,3-thiazolidine]-malondiamide;
starting from the appropriate 3-carboxyacethyl-1,3-thiazolidine.

EXAMPLE 10

Dicyclohexylcarbodiimide (5.34 g) is added to a mixture of 4-methyl-piperazine (2.82 g) and (R,S)-2-(2-methoxy-phenoxymethyl)-3-carboxyacetyl-1,3-thiazolidine (8 g) in dry ethyl acetate (80 ml). The mixture is heated for 3 hours at 40° C. and after cooling the precipitate of N,N-dicyclohexylurea is discarded by filtration. The filtered organic phase is washed in aqueous 2N H₂SO₄ for several times and then it is discarded. The combined acid aqueous extracts are alkalinized to pH 9, extracted with ethyl acetate to give, after the usual work-up, 7 g of N-(4-methyl-piperazin-1-yl), N-[(R,S)-2-(2-methoxyphenoxymethoxy)-1,3-thiazolidine]-malondiamide, m.p. 78°–80° C.

Using the same procedure, the following compounds are prepared:
N-piperidin-N'-[(R,S)-2-(2-methoxy-phenyl)-ethyl-1,3-thiazolidine]-malondiamide;
N-piperidin-N'-[(R,S)-2-(2-methoxy-phenoxymethyl)-1,3-thiazolidine]-malondiamide;
N-morpholin-N'-[(R,S)-2-(2-methoxy-phenoxymethyl)-1,3-thiazolidine]-malondiamide;
N-morpholin-N'-[(R,S)-2-(2-methoxy-phenylthiomethyl)-1,3-thiazolidine]-malondiamide;
N-[4-benzyl-piperazin-1-yl],N-[(R,S)-2-(2-methoxyphenoxymethyl)-1,3-thiazolidine]-malondiamide;
N-(4-diphenylmethyl-piperazin-1-yl),N-[(R,S)-2-methoxy-phenoxymethyl)-1,3-thiazolidine]-malondiamide;
N-[4-bis-(4-fluorophenylmethyl)-piperazin-1-yl],-N-[(R,S)-2-(2-methoxyphenoxymethyl)-1,3-thiazolidine]-malondiamide;
N-(4-hexahydrobenzyl-piperazin-1-yl),N-[(R,S)-2-(2-methoxy-phenylthio-methyl)-1,3-thiazolidine]-malondiamide, starting from the appropriate 3-carboxy-acetyl-1,3-thiazolidine by reaction with the appropriate amine.

EXAMPLE 11

Diketene (5 ml) is added dropwise to a stirred solution of (R,S)-2-(2-methoxy-phenoxymethyl)-1,3-thiazolidine (4.5 g) in 50 ml of acetone, cooled at 0° C. The mixture is stirred for one hour at 0° C. and for two hours at 15°–18° C. After dilution of the reaction mixture with 10 ml of 5% aqueous NaHCO₃ and removal of the excess acetone under vacuum, the residue is partitioned between water and ethyl acetate (20:60).

The organic phase is separated and washed with aqueous 0.5 N H₂SO₄. After solvent removal in vacuum, the oily residue (6 g) is purified by chromatography on SiO₂ (100 g, eluents: hexane-ethyl acetate 2:1), to give 4.2 g of (R,S)-2-(2-methoxy-phenoxymethyl)-3-(3-oxo-butanoyl)-1,3-thiazolidine, m.p. 61°–63° C. (from ethyl ether).

EXAMPLE 12

A solution of 3-β-pyridyl-3-oxo-propanoic acid (0.165 g) in 4 ml tetrahydrofuran is added to a solution of carbonyldiimidazole (0.18 g) in 4 ml tetrahydrofuran and stirred for 25 minutes at 5°–10° C. A solution of (R,S)-2-(2-methoxy-phenoxymethyl)-1,3-thiazolidine (0.2 g) in tetrahydrofurane (5 ml) is added dropwise to the mixture, that is left overnight at room temperature. After removal of the solvent under vacuum, the residue is adsorbed on SiO₂. By elution with hexane-ethyl acetate (2:1), 0.28 g of (R,S)-2-(2-methoxy-phenoxymethyl)-3-(3-β-pyridyl-3-oxopropanyl)-1,3-thiazolidine are obtained.

Using the same procedure, the following compounds are
(R,S)-2-(2-methoxy-phenoxymethyl)-3-(3-phenyl-3-oxo-propanyl)-1,3-thiazolidine;
(R,S)-2-(2-methoxy-phenylthiomethyl)-3-(3-phenyl-3-oxo-propanoyl)-1,3-thiazolidine;
(R,S)-2-(2-methoxy-phenoxymethyl)-3-(3-cyclohexyl-3-oxo-propanyl)-1,3-thiazolidine;
(R,S)-2-(2-methoxy-phenyl-ethyl)-3-(3-cyclohexyl-3-oxo-propanyl)-1,3-thiazolidine,
by reaction of the appropriate 1,3-thiazolidine with the appropriate β-keto-acid.

EXAMPLE 13

A solution of (R,S)-2-(2-methoxy-phenoxymethyl)-3-ethoxycarbonyl-acetyl- 1,3-thiazolidine (1 g) in a 33% methylamine solution in ethanol (8 ml) is heated for 6 hours at 35°–40° C. After cooling and dilution with a 30% NaH₂PO₄ aqueous solution (20 ml), the mixture is extracted with dichloroethane (2×15 ml). The combined organic phases are washed with aqueous 2N H₂SO₄, aqueous NaHCO₃ and water and anidrified on Na₂SO₄. After evaporation, the residue is crystallized from ethyl acetate to give 0.8 g of N-methylamino-N-[(R,S)-2-(2-methoxy-phenoxymethyl)-1,3-thiazolidine]-malondiamide, m.p. 136°–138° C.

EXAMPLE 14

A solution of diethylaminoethylamine (10.3 ml) and (R,S)-2-(2-methoxyphenoxymethyl)-3-ethoxycarbonylacetyl-1,3-thiazolidine (5 g) in ethanol (50 ml) is refluxed for 48 hours. After removal of the solvent, the residue is partitioned between ethyl acetate and aqueous H₂SO₄. The organic phase is discarded, the combined acid aqueous phases are alkalinized to pH 8.5 and extracted with ethyl acetate. The combined organic extracts, after usual work-up, are evaporated to dryness and the residue is crystallized from ethyl ether to give 2.1 g of N-(diethylaminoethyl), N'-[(R,S)-2-(2-methoxyphenoxymethyl)-1,3-thiazolidine]-malondiamide, m.p. 63°-66° C.

EXAMPLE 15

A solution of ethylmalonylchloride (1.5 g) in ethyl acetate (5 ml) is added to a vigorously stirred mixture of a solution of cyclohexylmethylamine (1.13 g) in ethyl acetate (20 ml) and of a solution of 1.01 g of $KNCO_3$ in water (5 ml). After one hour, the aqueous and organic phases are separated. After washing of the organic phase with water and removal of the solvent, a solution of the crude residue in ethanol (20 ml) is treated with aqueous 1N NaOH (10 ml) and for one hour.

After concentration to a small volume, the mixture is diluted with water and extracted with ethyl acetate. The extracts are discarded, and the aqueous phase is acidified to pH 2 with 37% aqueous HCl and extracted with ethyl acetate. The combined organic extracts are washed with water and evaporated to dryness to give 2.1 g of N-methyl-N-cyclohexyl-monomalon-diamide.

A solution of this compound in anhydrous tetrahydrofuran (20 ml) is treated at 0° C. with 2 g of carbonyldiimidazole, stirred for one hour and then after addition of 2.2 g of (R,S)-2-(2-methoxyphenoxymethyl)-1,3-thiazolidine, the mixture is stirred for 3 hours.

After removal of the solvent, the residue is adsorbed on a silica gel column; by elution with hexane/ethyl acetate (2:1), 3.45 g of N,N-cyclohexyl, methyl-N'-[(R,S)-2-(2-methoxy-phenoxymethyl)-1,3-thiazolidine]-malondiamide are obtained.

EXAMPLE 16

Male guinea pigs (400–450 g) are anaesthetized with ethylurethane (i.p.) and pancuronium bromide (i.v.): the trachea is cannulated and the lungs are ventilated at constant volume by connection with "Rodent respirator" Basile apparatus mod. 7025. The pulmonary inflation pressure (PIP) is measured by connection to a sidewarm of the tracheal cannula of a Bell and Howell pressure transducer (mod. P 17570) that is connected to a Beckmann (mod. R 611) dynograph. The right jugular vein is catheterized for i.v. injection of autacoids and drugs. The pharmacological experiment starts with the treatment of the animal with the autacoids (for example acetylcholine by i.v. route in the interval 2.5–10 mcg/kg) in order to induce a reversible bronchoconstruction response, measured by an increase of the pulmonary inflation pressure (PIP). This increase is recorded and it is considered to represent the basal value of the animal bronochoconstrictor response to the challenge with the autacoid.

The animal is then actively exposed for a 10 minutes time period to the tobacco smoke of alighted cigarette (directly inspired by the animal). Afterwards the animal is challenged again with the autacoid, using the dosage previously injected for evokating the basal bronchoconstrictor response. The novel challenge induces an exacerbate bronochoconstrictory response and the airway hyper-reactivity is measured as the differential increase in the PIP after tobacco smoke exposure in respect to the basal value. The challenge may be repeated in the time, (2–3 hours after smoke exposure, too) until reproducible hyper-reactive responses are obtained or at different time from tobacco exposure.

At the end of the experiment and/or at a desired time after smoke exposure, the animal is disconnected, and the broncho-alveolar contents are examined by lavages, injecting in the trachea physiological alkaline solutions (10 ml×3 times). These BAL fluids are combined, centrifuged for 15 minutes at 150 g to give pellets that are suspended in physiological saline (1 ml). The total cell number of BAL fluid is counted in a Burcher camera.

Differential cell counts are made from centrifugated preparations stained with Diff-Quick® counting at least 300 cells for each sample and the % number of epithelial cells, eosinophils, neutrophils, lymphocytes and macrophages are determined.

A substance may be administered by i.v., oral, subcutaneous or intramuscular route at different times before tobacco smoke exposure. A compound is considered effective when it is able to prevent almost completely the exacerbate differential increase in the PIP and normalize the BAL cell cytologic pattern at the same dose level.

Differential increases of the pulmonary inflation pressure over the basal value after autacoid challenges, ranging from 150–200% are observed after smoke exposure in the animal control group (i.e. in the absence of any pharmacological treatment).

Drug treatment may be performed using different routes: intravenous, oral, subcutaneous and/or intramuscular; the substances may be administered at different times before smoke exposure and at different dose levels.

Dose related responses have been determined for reference drugs such as 6β-methyl-prednisolone-21-hemisuccinate sodium salt (6MPHE, by i.m. route, 7 hrs. b.s.l.), sodium dichromoglycate (DSCG, by i.m. route, 2 hrs. b.s.e.) and salbutamol (by i.v. route, 20 minutes before smoke exposure); the results reported in table 4, are expressed as % protection from hyperreactive reaction. A 50% protection means that in the treated animals the differential increase of the PIP of the 50% of the increase of the PIP in the control animal group (6 animals for group).

TABLE 4

| 6MPHE | | DSCG | | Salbutamol | |
|---|---|---|---|---|---|
| mg/kg | % protect. | mg/kg | % protect. | mg/kg | % protect. |
| 50 | 100 | 100 | 100 | | |
| 25 | 85 | 50 | 64 | 5 | 90 |
| 10 | 65 | 25 | 27 | | |

The compound (R,S)-2-(2-methoxyphenoxymethyl)-3-ethoxycarbonylacetyl-1,3-thiazolidine when administered by different routes 2 hours before smoke exposure appears to be highly effective in this pharmacological model. The results obtained with this compound and with other compounds of the invention are reported in Table 5.

TABLE 5

| Substance | Dose mg/kg | Route | % protection |
|---|---|---|---|
| 1 | 60 | o.s. | 96 |
| | 10 | i.m. | 95 |
| | 1 | i.v. | 100 |
| 2 | 1 | i.v. | 90 |
| | 60 | o.s. | 30 |

TABLE 5-continued

| Substance | Dose mg/kg | Route | % protection |
|---|---|---|---|
| 3 | 5 | i.v. | 100 |

1) (R,S)-2-(2-methoxyphenoxymethyl-3-ethoxycarbonylacetyl-1,3-thiazolidine;
2) (R,S)-2-(2-methoxyphenoxymethyl)-3-carboxyacetyl-1,3-thiazolidine;
3) N-pyridylmethyl, N-[2-(2-methoxyphenoxymethyl)-1,3-thiazolidine]-malondiamide.

We claim:

1. Compounds of formula I:

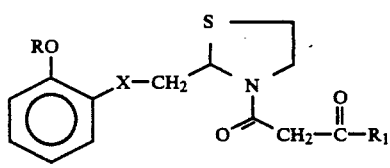

(I)

wherein:

R is hydrogen, a linear or branched $C_1$-$C_4$-alkyl, allyl or propargyl;

X is O, $CH_2$ or S;

$R_1$ is selected in the group of —$(CH_2)_n$Ra, hydroxy, —O—$(CH_2)_n$Ra, —NRbRc, —NHc$(CH_2)_m$—NRbRc;

Ra is hydrogen, a linear or branched $C_1$-$C_4$-alkyl, phenyl, p-methoxy-phenyl, 3,4,5-trimethoxyphenyl, B-pyridyl, cyclopentyl or cyclohexyl;

Rb and Rc, that can be the same or different are selected independently in the group of hydrogen, linear or branched $C_1$-$C_4$-alkyl, cyclohexyl cyclopentyl, benzyl, hexahydrobenzyl, $\alpha,\beta$ or $\gamma$-pyridylmethyl or Rb and Rc taken together with the N atom to which they are bound can form a morpholino, piperidino or piperazino residue for formula Rd—N($CH_2$—$CH_2$)$_2$—N— wherein Rd is hydrogen, linear or branched $C_1$-$C_4$-alkyl, benzyl, hexahydrobenzyl, $(C_6H_5)_2$CH—, (p—F—$C_6H_4$)$_2$CH or B-pyridylmethyl;

m is zero or an integer from 1 to 3 and n is 2 or 3.

2. Compounds according to claim 1 wherein X is oxygen.

3. Compounds according to claim 1 wherein R is methyl.

4. Compounds according to anyone of claims 1–3 wherein $R_1$ is selected in the group of methyl, ethoxy, hydroxy, aminomethyl, diethylamino-ethylamino, 4-methyl-piperazino, B-pyridylethylamino.

5. An antitussive agent comprising a compound of claims 1, 2 or 3.

6. Pharmaceutical compositions comprising as an active principle a compound of claim 1, 2 or 3 and a pharmaceutically acceptable carrier.

7. A method of inhibiting coughing in a patient in need of treatment for coughing, comprising administering to said patient a pharmaceutically effective amount of a compound of claims 1, 2 or 3.

* * * * *